US007659980B1

(12) United States Patent
Mitchell et al.

(10) Patent No.: US 7,659,980 B1
(45) Date of Patent: Feb. 9, 2010

(54) NEPHELOMETRIC TURBIDITY SENSOR DEVICE

(76) Inventors: Herbert Leckie Mitchell, 656 Independence Valley Dr., Grand Junction, CO (US) 81507; Steven Henry Mersch, 1864 Dayton Pike, Germantown, OH (US) 45327

(*) Notice: Subject to any disclaimer, the term of this patent is extended or adjusted under 35 U.S.C. 154(b) by 0 days.

(21) Appl. No.: 12/313,730

(22) Filed: Nov. 24, 2008

(51) Int. Cl.
*G01N 21/00* (2006.01)
(52) U.S. Cl. .................................. 356/339; 356/338
(58) Field of Classification Search ............. 356/339, 356/342
See application file for complete search history.

(56) References Cited

U.S. PATENT DOCUMENTS

| | | | | |
|---|---|---|---|---|
| 3,880,526 A | * | 4/1975 | Kobayashi et al. | 356/442 |
| 4,198,161 A | * | 4/1980 | Larson | 356/339 |
| 4,740,709 A | | 4/1988 | Leighton et al. | |
| 5,059,811 A | * | 10/1991 | King et al. | 250/573 |
| 5,067,814 A | * | 11/1991 | Suzuki et al. | 356/339 |
| 5,231,378 A | | 7/1993 | Dennis | |
| 5,305,093 A | * | 4/1994 | Dosmann | 356/435 |
| 5,331,177 A | | 7/1994 | Kubisiak et al. | |
| 5,446,544 A | | 8/1995 | Beers | |
| 5,467,187 A | * | 11/1995 | Beers | 356/243.2 |
| 5,475,486 A | * | 12/1995 | Paoli | 356/246 |
| 5,828,458 A | | 10/1998 | Taylor | |
| 5,831,727 A | | 11/1998 | Stream | |
| 5,872,361 A | | 2/1999 | Paoli | |
| 5,912,737 A | * | 6/1999 | Bannerjee et al. | 356/364 |
| 6,307,630 B1 | | 10/2001 | Banerjee | |
| 6,831,289 B1 | | 12/2004 | Preikszas | |
| 6,842,243 B2 | | 1/2005 | Tokhtuev et al. | |
| 6,894,778 B2 | | 5/2005 | Palumbo et al. | |
| 7,142,299 B2 | * | 11/2006 | Tokhtuev et al. | 356/338 |
| 7,430,043 B1 | * | 9/2008 | Evans | 356/244 |

* cited by examiner

*Primary Examiner*—Roy Punnoose

(57) ABSTRACT

Describes a nephelometric turbidity sensor device which embodies: methods for: (a) attenuation of entrained air, (b) attenuation of bubbles, (c) attenuation of scattered light (d) interchangeable light sources with automatic indexing of algorithms (e) anti-fog windows and (f) verification of operation by self-check and (g) self-calibration.

15 Claims, 14 Drawing Sheets

NEPHELOMETRIC TURBIDITY SENSOR DEVICE

TECHNICAL FIELD

Nephelometric turbidimeters are used to monitor on-line streams in water treatment plants, waste water treatment plants, industrial process streams and in other industries requiring detection of particle concentration in fluids. The differing wavelengths of the light-source beams provide detection of different ranges of particles in the concentration.

BACKGROUND

Turbidity comes from the Greek word turbid while nephelometric is the Greek word for cloud. In water treatment plants the required detection limit is approximately one part per million of particles with a detectable change of one part per billion of particles and is read in Nephelometric Turbidity Units, NTU. The specifications required for monitoring of water is set by each country, but all are similar in their quality control characteristics and performance. The cloudiness is caused by suspended solids in the fluid which may be organic material, clay, sand or other particulate matter. Bubbles are also seen as a particle and must be eliminated from the equation. In water treatment plants this measurement provides: (1) a measurement of filter effectiveness and (2) a surrogate method for determining the level of microbial contaminates embedded in the particulate matter in the incoming raw water and any microbial remnants in the filtered water. The greater the concentration of particles in the fluid, or turbidity, the higher the level of microbial contaminates embedded in the particles and the higher the required level of disinfection procedures. Treatment water plants walk a thin line between too little disinfection in protecting the community from harmful microbes and too much disinfection causing harm from disinfection by-products. Nephelometric turbidity is the EPA workhorse of all water treatment plants.

There are world-wide standard specifications for the measurement of turbidity in water treatment: (1) The USEPA 180.1 Nephelometric Method (2) 2130B Standard Methods for the Examination of Water and Waste Water and (3) the ISO 7027 International Standard Water Quality Determination of Turbidity 1999-12-15, (4) Hach 10133, (5) GLI Method II, (6) Mitchell Method M5331 LED, and (7) Mitchell Method M5271 laser. All specifications measure the intensity of scattered light from suspended particles in the fluid having a refractive index different from that of the sample fluid, measured at a 90 degree angle to the path of the incident light.

In order to satisfy the various wavelength requirements specified by different government agencies, a number of light sources have been EPA approved for nephelometric turbidity measurement and reporting:

| USEPA 180.1-1 | Incandescent | 2200-3000K Original |
| USEPA 180.1-2 | LED | 860 nm GLI 4-beam |
| USEPA 180.1-3 | Laser | 660 nm photomultiplier tube |
| USEPA 180.1-4 | LED | 525 nm Mitchell Method M5331 |
| USEPA 180.1-5 | Laser | 660 nm Mitchell Method M5271 |
| ISO 7027 basic | LED | 860 nm International |
| ISO 7027 alternate | LED | 550 nm International |

Each of these Methods has unique specifications. U.S. Pat. No. 7,142,299 states that each light source must have a sensor source receiver measuring voltages to detect differences in light sources, which are factory preset in order to determine if an LED or incandescent lamp is in use. It distinguishes type but not wavelength. In all current instrumentation, there is no design allowing for a plug-in method of exchanging only the light sources in a single sensor body or for automatically adjusting the system for matching algorithms to both source type and wavelength. The same patent also describes a sensor unit mounted on the cover inside the chamber. This arrangement is used by AquaSensor.

Many instruments either suspend the light source directly above the fluid with the scattered light detector submerged U.S. Pat. No. 6,307,630 or transmit and receive signals through a transparent cuvette which contains the fluid U.S. Pat. No. 5,446,544 or have transparent surfaces directly immersed in a fluid U.S. Pat. No. 7,142,299B2. Any difference in temperature between the fluid and interior of the sensor will result in fogging of the windows if any moisture is present. Efforts to control the moisture in the atmosphere behind the windows include use of desiccant dryers or fans U.S. Pat. No. 5,446,544. Desiccants are ineffective after a short period of time while other drying devices such as fans are unwieldy, only partially effective and expensive. There are no devices using a multiple, sealed, window construction for eliminating fogging in this context.

In order to measure low nephelometric levels of turbidity, the signal received from the scattered particles must be as free of extraneous signals as possible. The scattered light bouncing around inside the chamber induces background noise which cannot be distinguished from the turbidity response to actual particles. Several approaches are commonly used to limit the unwanted reflections ranging from a simple black surface, wavelength dependent coatings, or light trap apertures through which a beam passes into an isolated area where unwanted light is partially absorbed U.S. Pat. No. 6,307,630. These traps require a complex shape and sufficient space to operate U.S. Pat. No. 6,831,289 with inverted or non inverted cones U.S. Pat. No. 5,872,361 and U.S. Pat. No. 6,894,778 or use of plain cones U.S. Pat. No. 5,231,378. None of these approaches eliminate the small amount of returning light which is scattered throughout the chamber, nor does it eliminate the initial reflections which were only partially absorbed. There are no instruments utilizing cone diffuser with a tapered, cylinder shaped housing. There are no instruments utilizing a combination of multiple absorbing and reflective elements to attenuate the source light beam.

For on-line instrumentation measuring turbidity levels, bubbles which are seen as particulate matter must be removed from the equation. There are two standard approaches to the elimination of entrained air and bubbles: (1) separating fluid that contains entrained air from fluid which does not carry entrained air and (2) holding the sensor housing under pressure, preventing bubbles from forming. The bubbles are caused by temperature increase, pressure decrease or by previously entrained gases. Current designs for removal or prevention of entrained air and bubbles may actually generate additional bubbles from out-gassing due to pressure decrease or temperature increase. Pressurized systems are unable to eliminate existing entrained air and bubbles, but may prevent additional bubbles from forming.

Separation of gases may be done by passing the fluid over protrusions at operating or atmospheric pressure. U.S. Pat. Nos. 5,831,727 and 5,331,177 describe the general method. However, there is the problem of reduced pressure causing out-gassing and possibly allowing a temperature rise by using a fluid colder than the utility environment, which inadvertently can allow warming and out-gassing of bubbles. Use of a chamber which can be kept under pressure but allows bubbles to rise and vent out an upper port is shown in U.S. Pat. No. 4,740,709; however, this method can allow measurement to take place in an area of stagnation, thus providing false readings. U.S. Pat. No. 5,475,486 describes a bubble trap for use in a cuvette type operation, but requires separate drain ports at the top and bottom of the container. This method cannot be operated under pressure and requires a transparent cuvette chamber. U.S. Pat. No. 5,059,811 incorporates a bubble trap with a dam diverter and multiple fluid passages to direct the fluid flow. There are no current devices using a combination of fluid under pressure and fluid separator plate to set up different flow paths for fluid containing bubbles and fluid not containing bubbles.

The EPA has two standards for calibration: (1) primary calibration for EPA reporting and (2) secondary calibration for internal plant verification. EPA reporting requires a monitoring response to detect changes in the fluid's turbidity to approximately one part per billion of suspended particles. Accurate responses at this level are difficult to sustain using current instrumentation. The EPA has a number of concerns about the stability of current nephelometric turbidimeters: the incandescent light source tends to drift in intensity, the electronic components trend to drift, while the scattered light receiver deteriorates over time. The large majority of field units are of this type. There are currently no automated methods for maintaining instrument stability from drift or verifying operation; there are some designs with feedback loops which stabilize only the light source U.S. Pat. No. 5,828,458. The approach described in U.S. Pat. No. 6,842,243 attempts to detect changes in operation by periodically transmitting reflected light from the back of the source window optics to a reflected area on the back of the scattered light window optics but does not consider changes in reflected light going into the scattered light receiver caused by fouling, fogging, finger prints, etc.

Several methods of using manually inserted calibration apparatus for secondary calibration are in use but all suffer difficulties. U.S. Pat. No. 5,467,187 shows a pulsed system varying the position of using sealed standards in a cuvette requiring a pump and complex plumbing. Variation in position of the floating standards and complex processing in the change in signal limit the repeatability of this method.

Because of these problems, the EPA mandates frequent re-calibration. However, calibration is time consuming, requires a skilled operator, and stoppage of the on-line monitoring process; it is expensive, complex, and produces high operator error. In addition, current methods of calibration require exposing the sample fluid to contamination from the outside. A number of efforts have been made to approach the specifications as closely as possible. U.S. Pat. No. 5,467,187 attempts to use a water pulse with a sealed cuvette bouncing multiple standards in the detection area. Because of variability in placement position and surface contamination of scratches, fouling, and complex processing of signal, the units' variability response limits its application as a replacement for manual calibration. U.S. Pat. No. 6,307,630 describes a method of periodically adding a sample of uncontrolled source light to the test fluid via mirrors, optical switch and polarized filters in the sensor, but does not compensate for source lamp variation or film build-up on the windows, or negate the fluid's turbidity reading during calibration. There are a number of manual reference blocks acceptable to the EPA for secondary calibration, but none are automatic or protected in its environment free of scratches and finger prints, and all leave the sample water exposed to contamination, and most importantly can not be used for primary calibration for EPA reporting.

While there has been some advancement in turbidity devices since the 1950s, there remains a need to improve over the art, bringing the EPA specifications closer to available technology. The EPA is highly cautious about granting new Methods for EPA reporting and will only do so if there is sufficient improvement in safety, accuracy and advanced technology to warrant the EPA approval process. The process takes about four years to complete.

SUMMARY

The present device known as a nephelometric turbidimeter provides a means of optically monitoring concentrations of solid particles in fluid through the attenuation of extraneous non-particle, electronically-processed signals which arise from entrained air, out-gassed bubbles and scattered light. The device maintains operating pressure and provides for removal of entrained air and bubbles using gravity with flow rate and using a single fluid separator plate for diverting heavier fluid free of bubbles from lighter, fluid with bubbles, from passing through the sensing volume. A combination of multiple absorbing and reflective elements is used in attenuating scattered light using its side walls embodying either a tapered cylinder or an inverted tapered cylinder in conjunction with a reverse cone shaped diffuser, or a cone shaped diffuser.

Built into the sensor body is also a means for mechanically interchanging light sources using a plug-in approach in a single sensor body with a means of automatically indexing the light source to the correct algorithm.

Because of the moisture laden atmosphere of treatment plants, the window modules in this device have multiple, sealed window and element construction in conjunction with a combination of mounting methods; a portion of the window module is molded into the frame while another portion of the window module uses moisture impervious adhesive, thus providing a moisture proof seal around all optical components. The multiple window and optical element module construction provides a dry zone between the external window and the optical elements in the same module preventing any fogging or moisture build up on the window in contact with the fluid.

The instant device also allows for verification of operating functions utilizing means for self-check and self-calibration. This system assures the operator that the instrumentation is operating efficiently and without error. Automated calibration reduces operator error; the instrument embodies two ways to automatically self-calibrate: one approach utilizes EPA secondary calibration by use of a moveable, solid calibration block of known calibration material built into the sensor head which can be automatically inserted into the external container in front of the sensor head and can be replaced yearly. It is designed to be impervious to finger prints, scratching, fogging and fouling. The second approach utilizes EPA primary calibration by use of an automatic, moveable calibration chamber which provides a close refractive index match between the calibration chamber and the sample water. The calibration chamber is inserted through the external container in the same manner as the solid calibration block and can be replaced on an annual basis. The combination of this refractive index matching and the use of a stable calibration standard material and stable positioning feature eliminate extraneous responses in the calibration reading and meets EPA specifications for primary reporting.

As part of the verification of operating functions, the present device embodies several means of providing self-check of the correct operation of the reference light detector, the reference light receiver, the scattered light detector, scattered light receiver and circuit board. The instrumentation provides a means to detect external window cleanliness using comparison data and a structure for self-check using a step of the source light or from a separate calibration source light.

It is an object to improve nephelometric turbidimeters.

It is an object to provide a nephelometer with interchangeable light source modules in the sensor body and to automatically adjust for the proper algorithm.

It is an object to provide a nephelometer with moisture proof construction having anti-fog properties for all external optical windows.

It is another object to provide a nephelometer with a means to remove entrained air and bubbles using a combination of keeping the fluid under pressure with separate flow paths for fluid with bubbles and fluid without bubbles using a fluid separator plate.

It is another object to fully attenuate all scattered light through a light trap comprising tapered cylinder shaped walls and cone configurations.

It is still another object to provide a nephelometer with both manual and automatic means of EPA primary and secondary calibration.

It is a further object to prove a nephelometer with a means of self-checking for correct operation of sensors and electronics.

Other objects and advantages will be apparent to those skilled in the art upon viewing the drawings and reading the detailed descriptions. These and various other advantages and features of novelty which characterize the device are pointed out with particularity in the claims.

FIGURE NUMBERS OF THE DRAWINGS WITH DESCRIPTION

Figure 1:
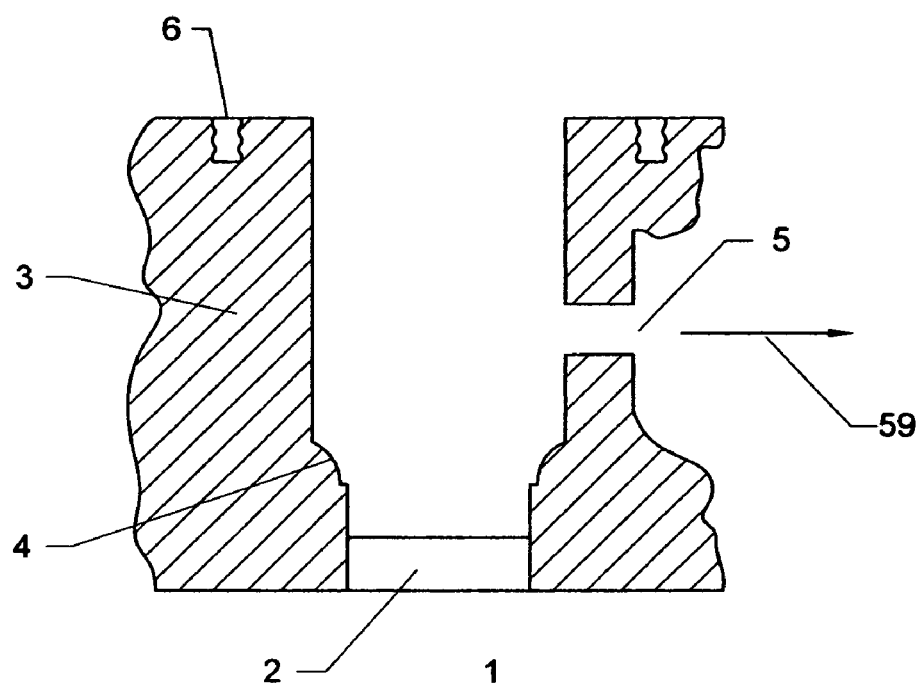
FIG. 1 depicts a section view of a portion of a sensor housing of the present invention.

REFERENCE NUMBERS WITH DESCRIPTION 1. fluid
2. sealed window module
2a. stepped window assembly
2b. tapered window assembly
2c. flat window assembly
3. sensor housing
4. mounting ring and guide female
5. sensor light path opening
6. threaded screw holes
7. lamp module housing
8. first optical element
9. filter
10. light source
11. drive circuitry
12. hole
13. mounting ring and guide male
14. light path opening
15. external window
16. moisture impervious adhesive
17. structural moisture impervious adhesive
18. second optical element
19. interior zone
20. stepped window
21. molded stepped window insert
22. tapered window
23. molded tapered window insert
24. molded flat window insert
25. flat window
26. source light beam
27. tapered cylinder, single piece
27S. supports
27W. walls
28. cone shaped diffuser, single piece
29. reverse tapered cylinder, two piece
29S. supports
29W walls
30. cone shaped diffuser, two piece
31. tapered cylinder, single piece
31S supports
31W. walls
32. reverse cone shaped diffuser, single piece
33. reverse tapered cylinder, two piece
33S. supports
33W. walls
34. reverse cone shaped diffuser, two piece
35. self calibration opening
36. connector
37. scattered light beam
38. particle
39. external container
40. inlet
41. self calibration cover 42. main outlet
43. sensing volume
44. bubble separator device
45. bubble free fluid
46. fluid containing bubbles
47. fluid separator plate
48. calibration chamber
49. seal
50. shaft
51. drive mechanism
52. signal path
53. electronic circuit board
54. wiper
55. solid calibration block
56. low refractive index walls
57. opening
58. calibration standard material
59. reference light path
60. attenuator
61. light path
62. reference light detector
63. reference light receiver
64. signal path
71. scattered light detector
72. scattered light receiver
73. signal path
74. signal path
75. lamp controller
76. calibration source light
77. light path
78. attenuator
79. light path
80. light path
81. attenuator
82. signal path
83. light path
2X. light source window module
2Y. scattered light detector window module
M1. light source module
2A. stepped window assembly
2B. tapered window assembly
2C. flat window assembly
T1. light trap, tapered cylinder and cone shaped diffuser
T2. light trap, reverse tapered cylinder and cone shaped diffuser
T3. light trap, tapered cylinder and reverse cone shaped diffuser
T4. light trap, reverse tapered cylinder and reverse cone shaped diffuser

DETAILED DESCRIPTION

Referring to the drawings, there are a number of embodiments set forth which will be described with respect to each relevant drawing wherein like numerals represent like components.

FIG. 1 depicts sensor housing 3 for a light source module M1 (see FIG. 2) is provided. A sealed window module 2 for sensor housing 3 prevents fluid 1 from entering lamp module housing 7. A female locking mounting ring and guide 4 guides the source module M1 into position which is light tight. The light source module M1 is locked into place by insertion of two screws (not shown) through holes 12 FIG. 2 in module M1 and which are secure to threaded screw holes 6. Sensor light path opening 5 in the sensor housing 3 and light path opening 14 of the light module M1 allows transmission light from light source 10 of reference light path 59.

Figure 2:
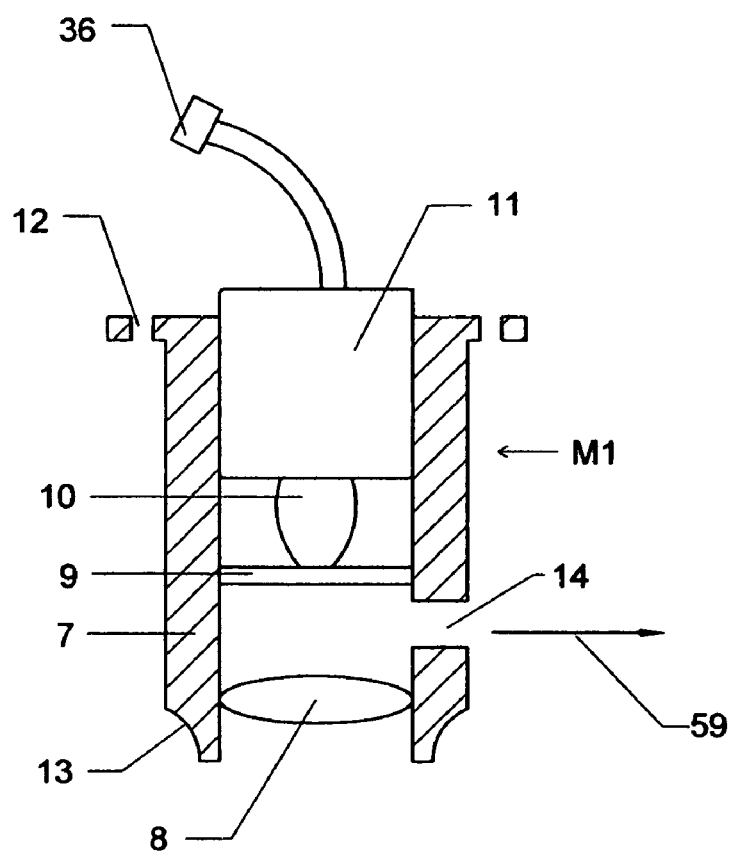
FIG. 2 depicts a section view of a light source and module of the present invention.

FIG. 2 depicts light module M1 is provided with a light source 10 of a type known to the art, held in lamp module housing 7, and includes operable associated drive circuitry 11. A filter 9 and a first optical element 8 are mounted in the lamp module housing 7 for use with poorly focused light sources. Light path opening 14 is provided for reference light path 59. A locking mounting ring and guide 13 guides the lamp module housing 7 into place. Once the lamp module housing 7 is so disposed, it is then locked in place by screws through holes 12 and the threaded holes 6. A light sample from light source 10 for other uses is directed out of the light path opening 14 and sensor light path opening 5 (FIG. 1.) The module M1 clips into place and is locked into place optically as well. The output cable and connector 36 is indexed so as to provide information to the monitor as to which of the algorithms to use with each specific and interchangeable light source 10.

Figure 3:
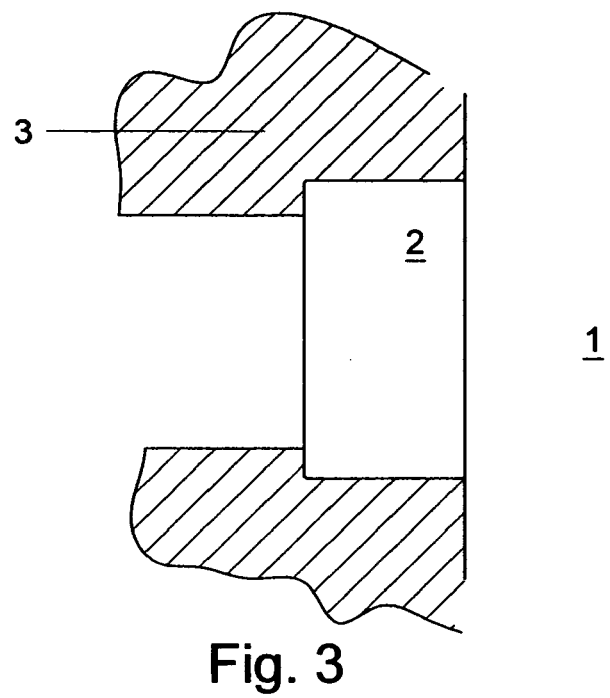
FIG. 3 depicts a section view of a sealed window module of the present invention.

FIG. 3 depicts anti-fog sealed window modules 2 in sensor housing 3 which are necessary because of moisture build-up and fogging because of differences in external fluid 1 temperature from internal air temperature of the sensor.

Figure 4:
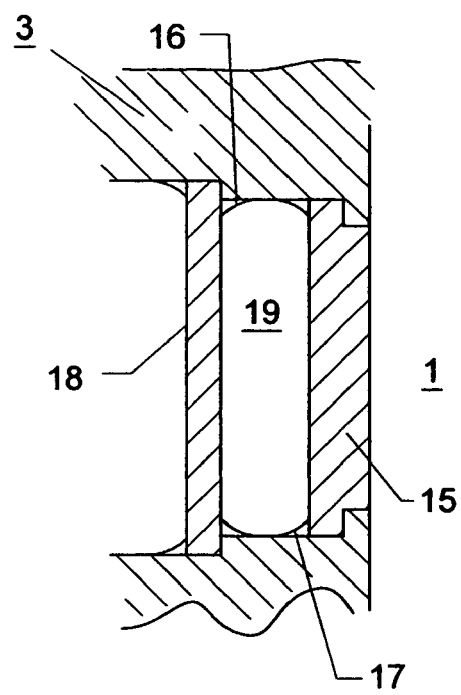
FIG. 4 depicts a section view of an adhesive mounting of a window module.

FIG. 4 depicts a method of installing an anti-fogging window module, including external mounted window 15 and second optical element 18, both being made of any transparent material, located in sensor housing 3. The external window 15 is held in place with structural moisture impervious adhesive 17. The interior zone 19 is sealed and is either a vacuum or filled with dry gas during assembly. The second optical element 18 is also sealed in place with a moisture impervious adhesive 16 into the sensor housing 3.

Figure 5:
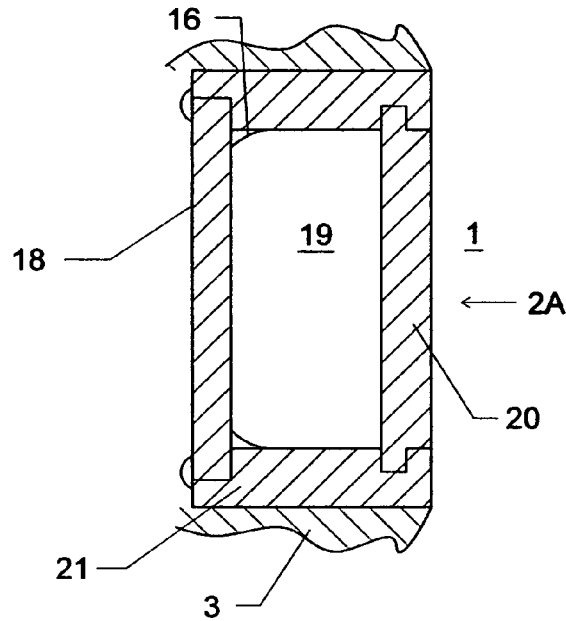
FIG. 5 depicts a section view of a stepped window module assembly.

FIG. 5 depicts a stepped window assembly 2A in which stepped window 20 is molded into insert 21. Stepped window 20 is any material that is transparent, such as glass, plastic, quartz, or sapphire. Stepped window 20 is flush with the molded stepped window insert 21 to prevent trapping bubbles from the fluid 1. The second optical element 18 is sealed in place with moisture impervious adhesive 16 before the assembly 2A is molded into the overall sensor housing 3 in place of the sealed window module 2 as seen in FIG. 1. The interior zone 19 between the stepped window 20 and the second optical element 18 is sealed and filled with dry gas or is a vacuum 19.

Figure 6:
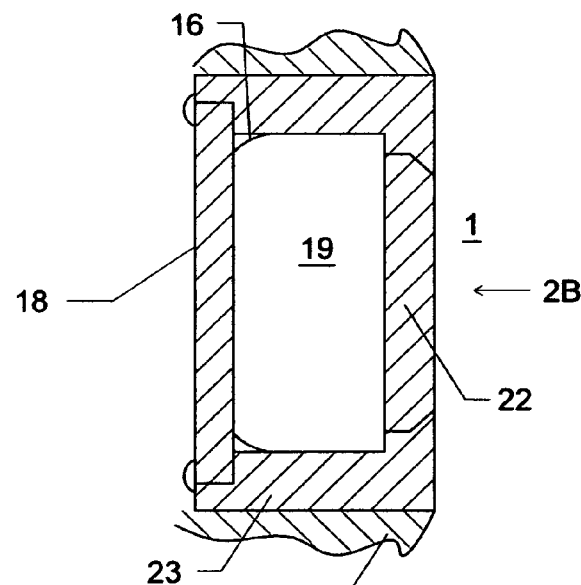
FIG. 6 depicts a section view of a tapered window module assembly.

FIG. 6 depicts a tapered window assembly 2B in which tapered window 22 is molded into tapered molded window insert 23. The tapered window 22 can be made of any material that is transparent such as glass, plastic, quartz or sapphire. The tapered window 22 is flush with the tapered molded window insert 23 to prevent trapping bubbles from the fluid 1. The second optical element 18 is sealed in place with moisture impervious adhesive 16 before tapered window insert assembly 2B is molded into the housing 3 in place of window module 2. Interior zone 19, between the tapered window 22 and the second optical element 18 is sealed and filled with dry gas or is a vacuum.

Figure 7:
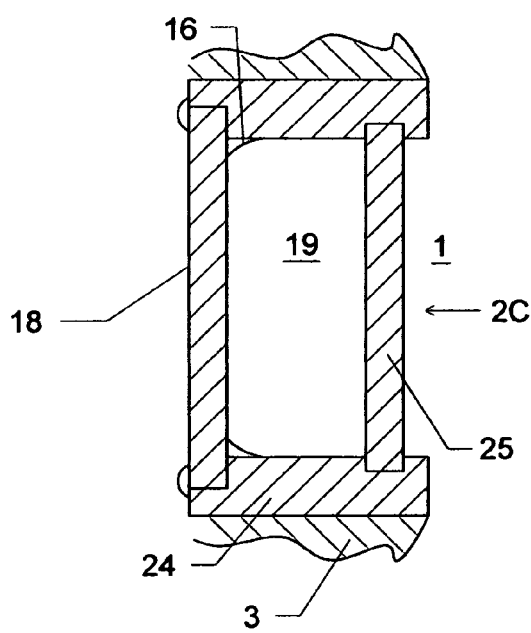
FIG. 7 depicts a section view of a flat window module assembly.
Figure 8:
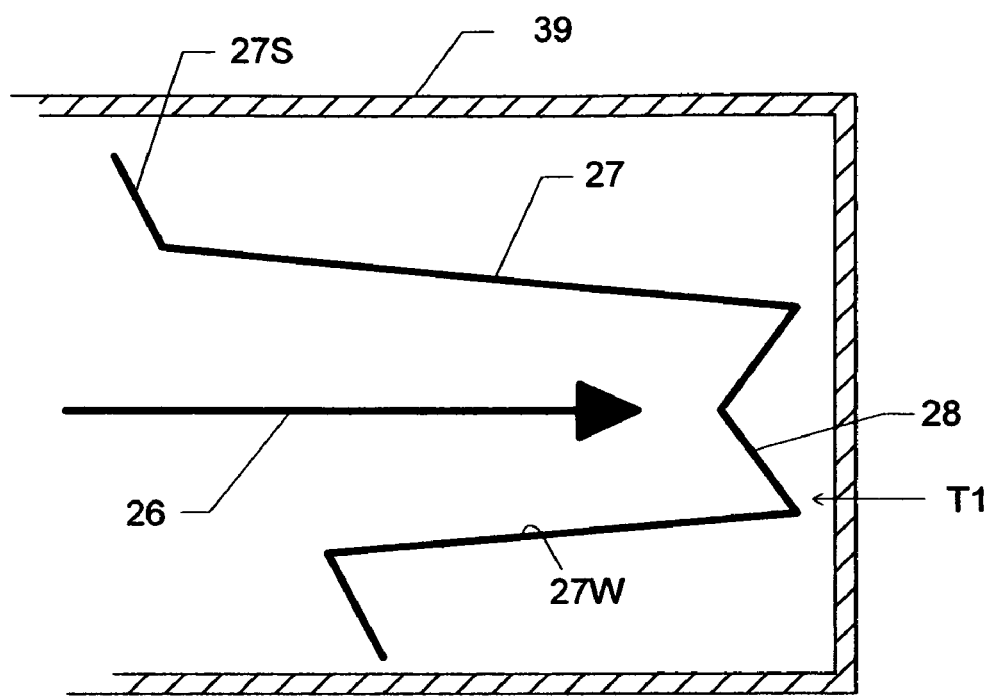
FIG. 8 depicts a section view of a cone diffuser and tapered cylinder light trap.

FIG. 7 depicts a flat window assembly 2C in which flat window 25 is molded into the molded flat window insert 24. The flat window 25 is made of any material that is transparent such as glass, plastic, quartz or sapphire. Flat window 25 is not flush and hence requires caution in use with various fluids 1 to prevent bubbles from collecting along the molded flat window insert rim 24. The second optical element 18 is sealed in place with moisture impervious adhesive 16 before the overall flat window assembly 2C is molded into the sensor housing 3 in place of window module 2. The interior zone 19 between the flat window 25 and the second optical element 18 is sealed and is dry gas filled or is a vacuum. Impervious FIG. 8 depicts a light trap T1 utilizing a combination of multiple absorbing and reflective elements mounted in the interior of external container 39 for use with turbidity monitoring requiring the attenuation of a source light beam 26. The exterior is a tapered cylinder 27, single piece, with supports 27S made of a non-reflective material of a type known to the art as rigid black plastic which forms an exterior of the trap T1. A cone shaped diffuser, single piece, 28, also made of a non-reflective material, absorbs the light and directs any remaining light at a steep angle onto the walls 27W of the tapered cylinder 27 with supports 27S.

Figure 9:
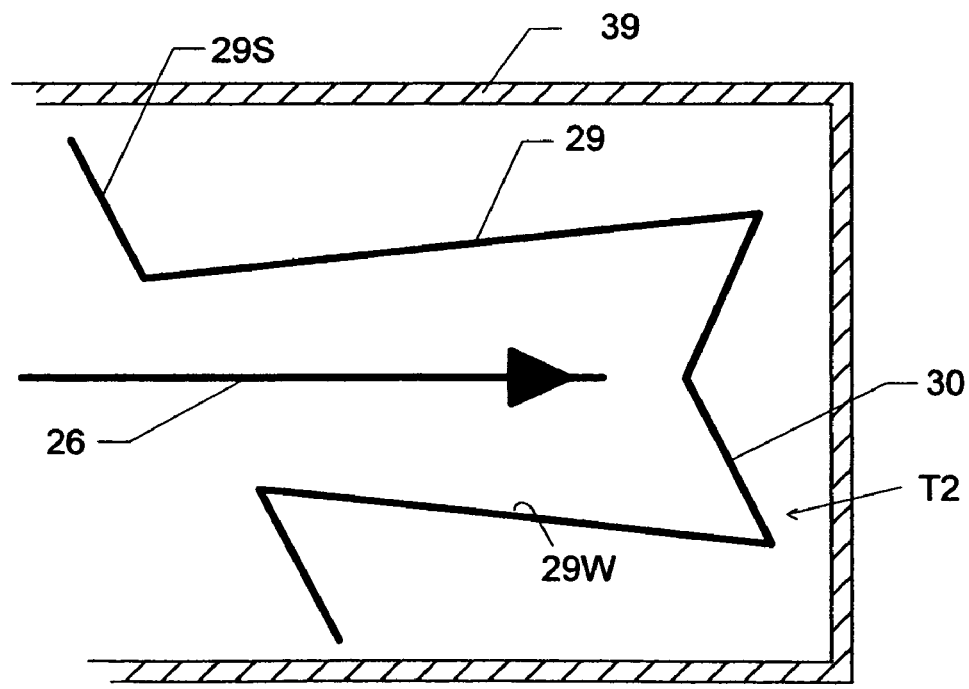
FIG. 9 depicts a section view of cone diffuser and reverse tapered cylinder light trap.

FIG. 9 depicts a light trap T2 utilizing a combination of multiple absorbing and reflective elements mounted in the interior of external container 39 for use with turbidity measurement requiring the attenuation of a source light beam 26. A reverse tapered cylinder, two piece 29 with supports 29S made of a non-reflective material and forms the exterior of the trap T2. A cone shaped diffuser, two piece 30 absorbs light and directs any remaining light at a steep angle onto the walls 29W of the reverse tapered cylinder 29 with supports 29S.

Figure 10:
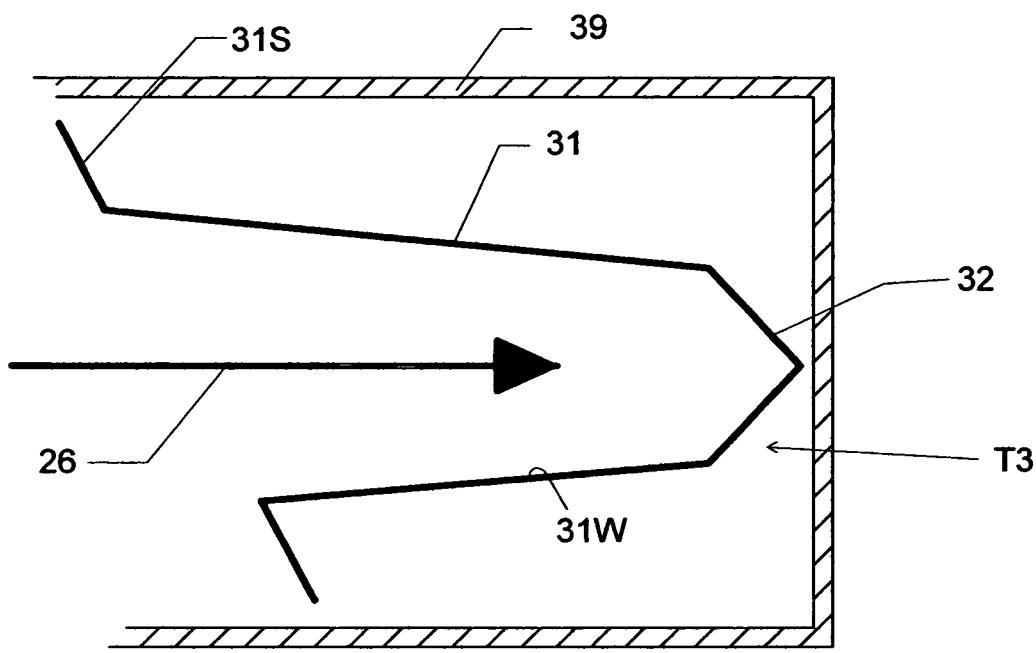
FIG. 10 depicts a section view of a reverse cone diffuser and tapered cylinder light trap.

FIG. 10 depicts a light trap T3 utilizing a combination of multiple absorbing and reflective elements mounted in the interior of external container 39 for use with turbidity monitoring instrumentation requiring the attenuation of a source light beam 26. A tapered cylinder, single piece, 31 with supports 31S, made of non-reflective material forms the exterior of the light trap T3. A reverse cone shaped diffuser, single piece, 32 absorbs and reflects any remaining light at the end of the tapered cylinder, single piece, 31 with supports 31S, allowing any remaining light to be reflected back onto the walls 31W many more times than by using a flat end.

Figure 11:
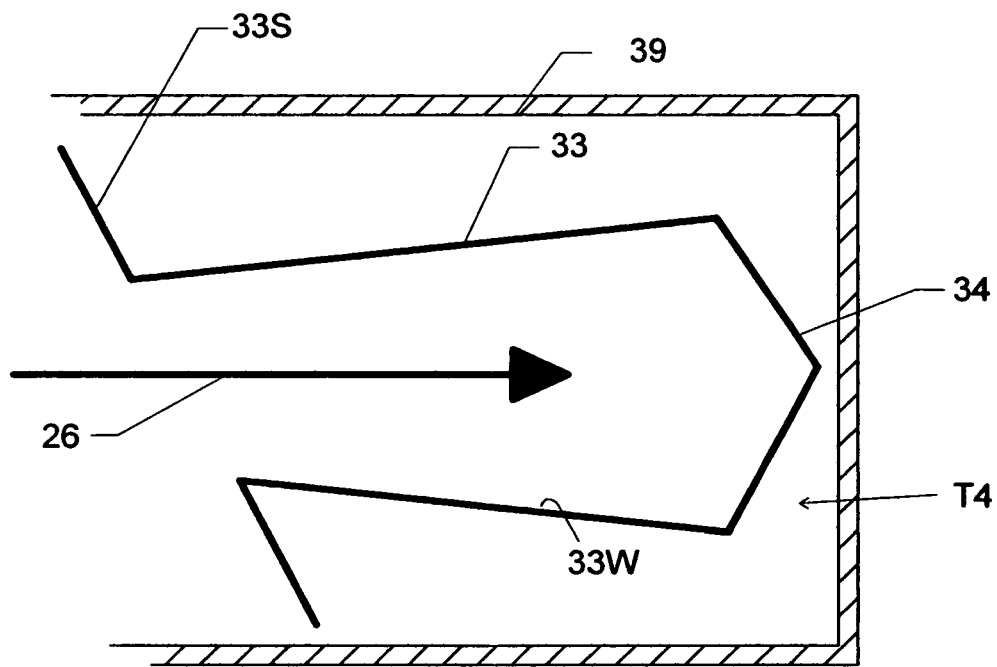
FIG. 11 depicts a section view of a reverse cone diffuser and reverse tapered cylinder light trap.

FIG. 11 depicts a light trap T4 utilizing a combination of multiple absorbing and reflective elements mounted in the interior of external container 39 for use with turbidity monitoring instrumentation requiring the attenuation of a source light beam 26. A reverse tapered cylinder, two piece, 33 with supports 33S, made of a non-reflective material forms the exterior of light trap T4. A reverse cone shaped diffuser, two piece, 34 at the end of the trap made of non-reflective material absorbs and reflects any remaining light on the walls 33W.

Figure 12:
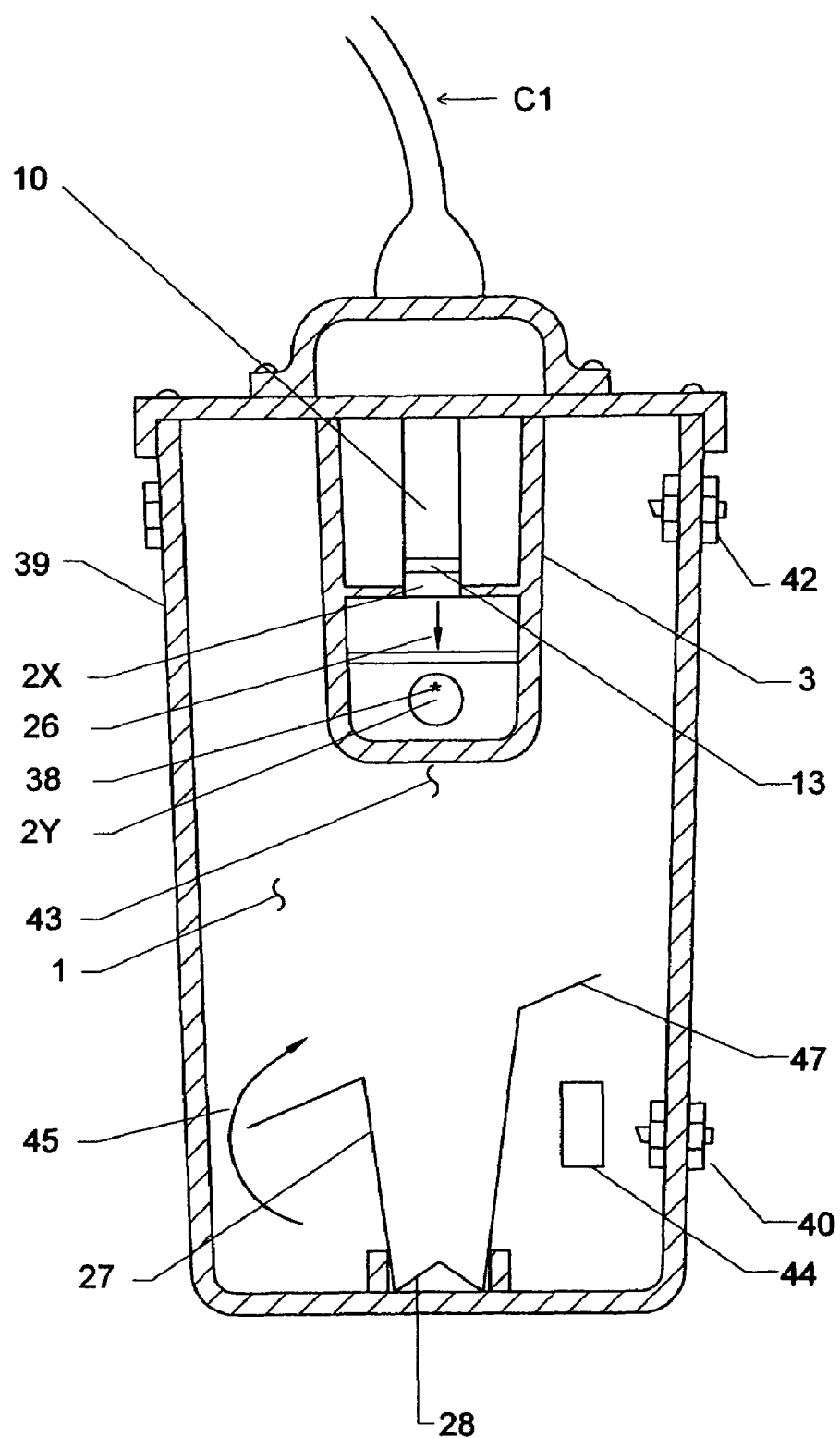
FIG. 12 depicts a section view of said nephelometer including sensor.

FIG. 12 depicts a section view of said nephelometer including sensor. Fluid 1 enters exterior container 39 at inlet 40 where it is directed against bubble separator device 44. The bubble free fluid 45 portion of fluid 1 is directed downward by fluid separator plate 47. The bubble free fluid 45 then flows through the sensing volume 43 and out through the main outlet 42. The source light beam 26 from light source 10 in lamp module 7 exits the sensor housing 3 through light source window module 2X and contacts particle 38 in sensing volume 43 of the bubble free fluid 45 generating scattered light beam 37, not shown. Scattered light beam 37, not shown, enters the sensor housing 3 through scattered light sensor window module 2Y. The remaining source light beam 26 continues onward entering the tapered cone light trap consisting of tapered cylinder 27 typical and cone diffuser 28 typical.

Figure 13:
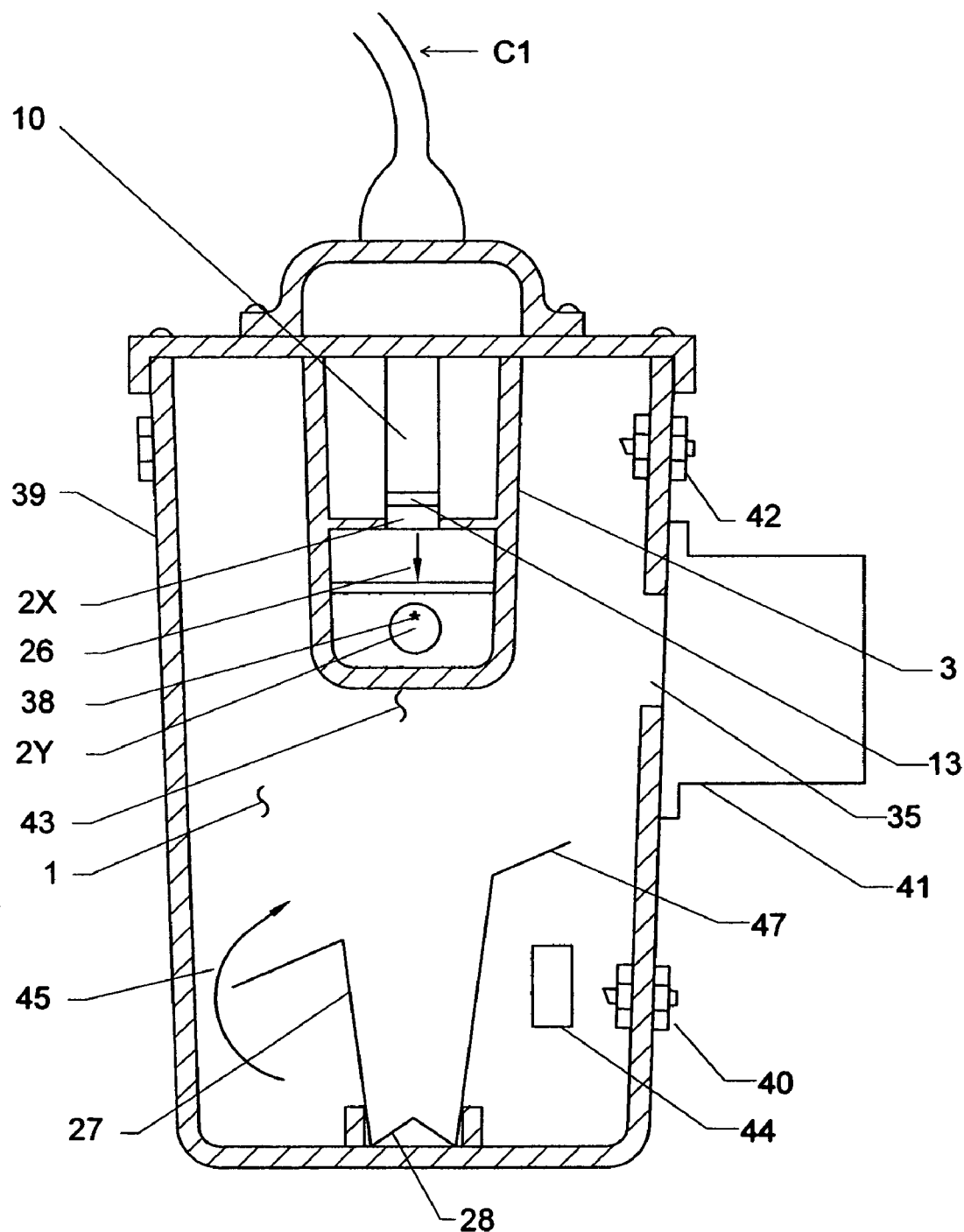
FIG. 13 depicts a section view of said nephelometer including sensor with self calibration installed.

FIG. 13 depicts section view of said nephelometer including sensor with self calibration installed. Fluid 1 enters exterior container 39 at inlet 40 and directed against bubble separator device 44. The bubble free fluid 45 portion of fluid 1 is directed downward by fluid separator plate 47. The bubble free fluid 45 flows through the sensing volume 43 and out through the main outlet 42. The source light beam 26 from light source 10 in lamp module 7 exits the sensor housing 3 through light source window module 2X and contacts particle 38 in the sensing volume 43 of the bubble free fluid 45 generating scattered light beam 37, not shown, Scattered light beam 37, not shown, enters the sensor housing 3 through scattered light sensor window module 2Y. The remaining source light beam 26 continues onward entering the tapered cone light trap consisting of tapered cylinder 27 typical and cone diffuser 28 typical. The self calibration cover 41 is mounted over the self calibration opening 35 in the external container 39.

Figure 14:
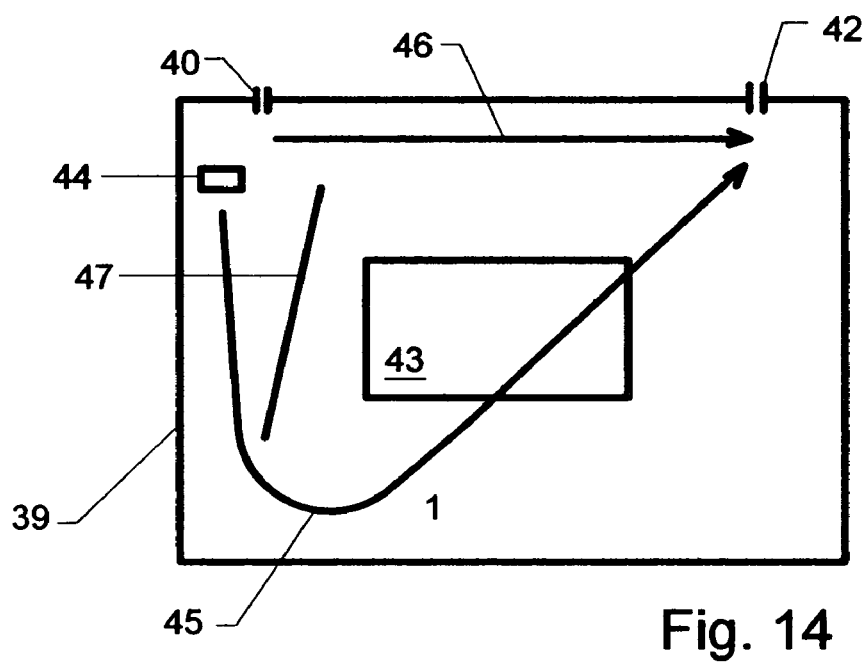
FIG. 14 depicts a section view of a bubble trap with fluid separator plate.

FIG. 14 depicts external container 39. The fluid 1 travels into an inlet 40 where it impacts a bubble separator device 44. The fluid containing bubbles 46 travel along the upper portion of the external container 39 and out of the main outlet 42. The higher density, bubble free, fluid 45 is directed downward by the fluid separator plate 47 to the lower portion of the external container 39 and then flows upward through the sensing volume 43 to the outlet 42.

Figure 15:
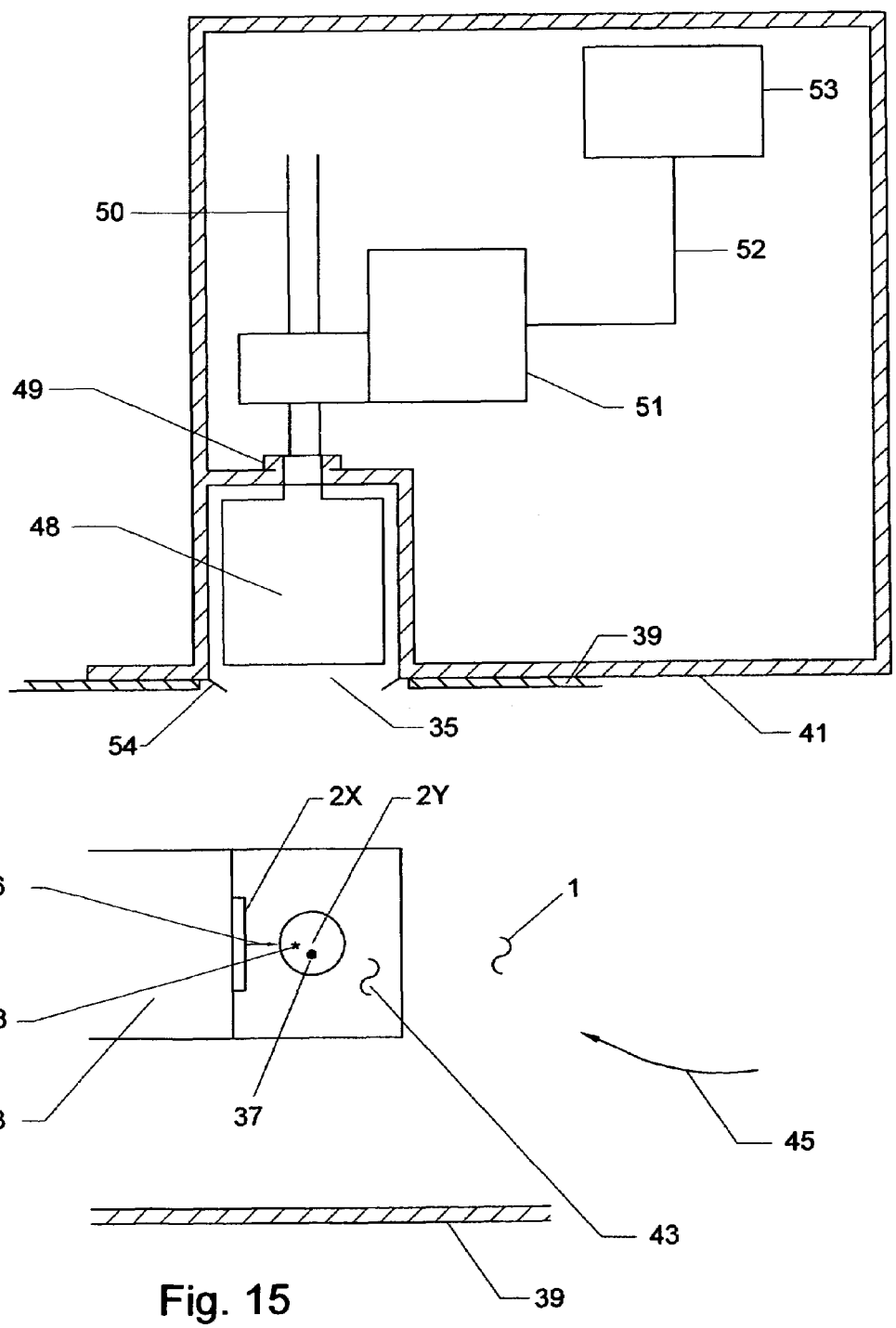
FIG. 15 depicts a section view of a self-calibration unit.

FIG. 15 depicts a nephelometric turbidity sensor for on-line use with an external container 39 holding fluid 1. The light source window module 2X directs source light beam 26 into the external container 39 where it is scattered by particles 38 suspended in the bubble free fluid 45 portion of fluid 1 and sensing volume 43 generating scattered light beam 37. The scattered light beam 37 is detected through scattered light sensor window module 2Y. A calibration chamber 48, of optional shape, is retracted out of the view of the source window module 2X and the scattered light detector window module 2Y. The calibration chamber 48 is mounted on a shaft 50 that goes through a seal 49 to prevent leakage and is connected to a drive mechanism 51. The drive mechanism 51 is periodically operated through signal path 52 from an electronic circuit board 53. The calibration opening 35 into the external container 39 has a wiper 54 surrounding it to clean the calibration chamber 48 when lowered into the sensing volume 43 between light source window module 2X and scattered window light module 2Y. The self-calibrate cover 41 supports the mechanism.

Figure 16:
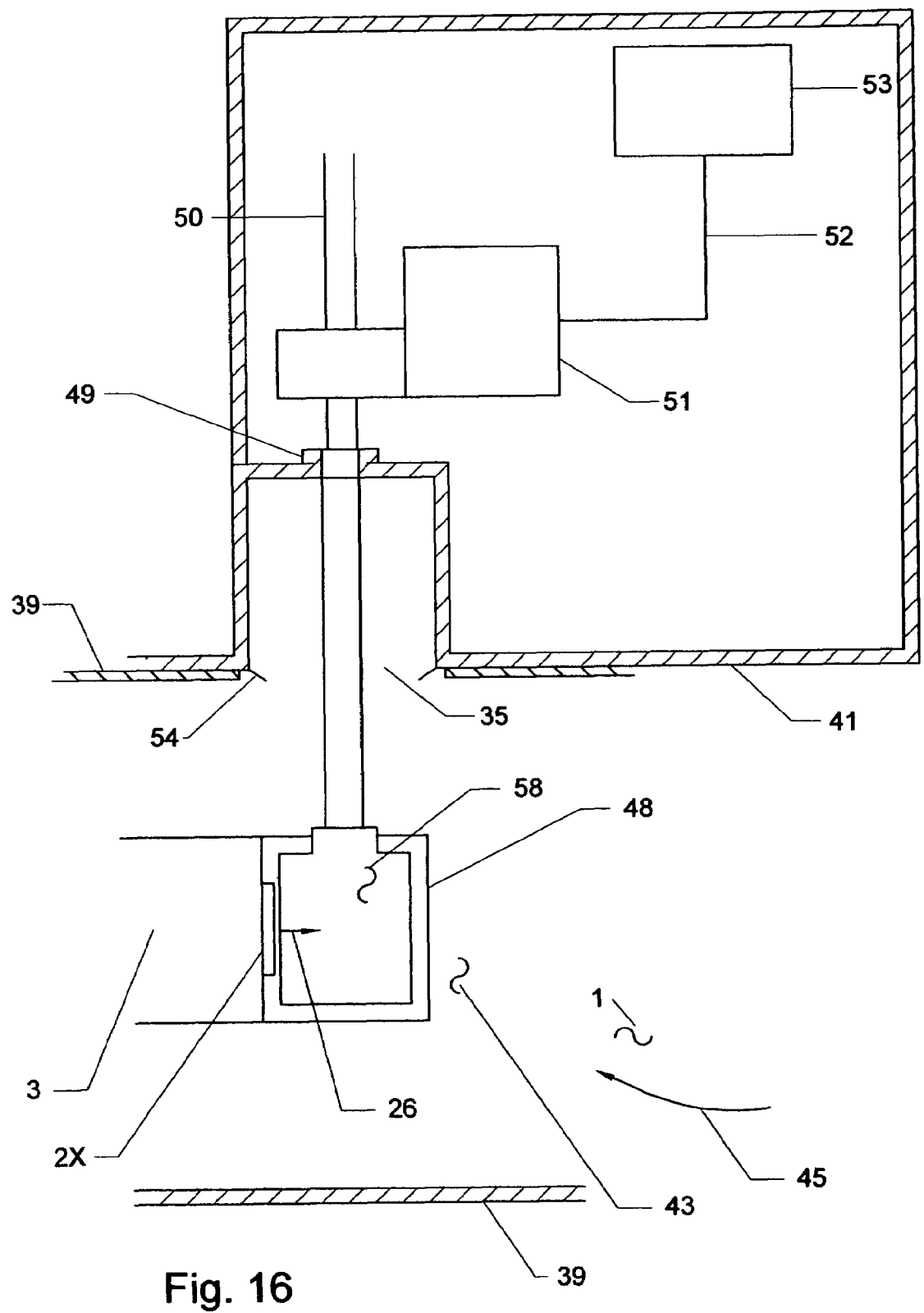
FIG. 16 depicts a section view of a calibration chamber in calibration position.

FIG. 16 depicts the nephelometric turbidimeter sensor with the optional shaped, calibration chamber 48 in the lowered position submerged into the sensing volume 43 of the fluid 1. The optional shaped, calibration chamber 48 is in close proximity to both the source light window module 2X and the scattered light detection window module 2Y. The optional shaped, calibration chamber 48 passed through the calibration opening 35 in the external container 39 has been wiped by the wipers 54 and is held in place by the shaft 50 passing through the seal 49. The drive mechanism 51 is operated by signal path 52 from the electronic circuit board 53. The self-calibrate cover 41 supports the mechanism. The source light beam 26 illuminates calibration material 58 rather than the fluid in sensing volume 43 of fluid 1.

Figure 17:
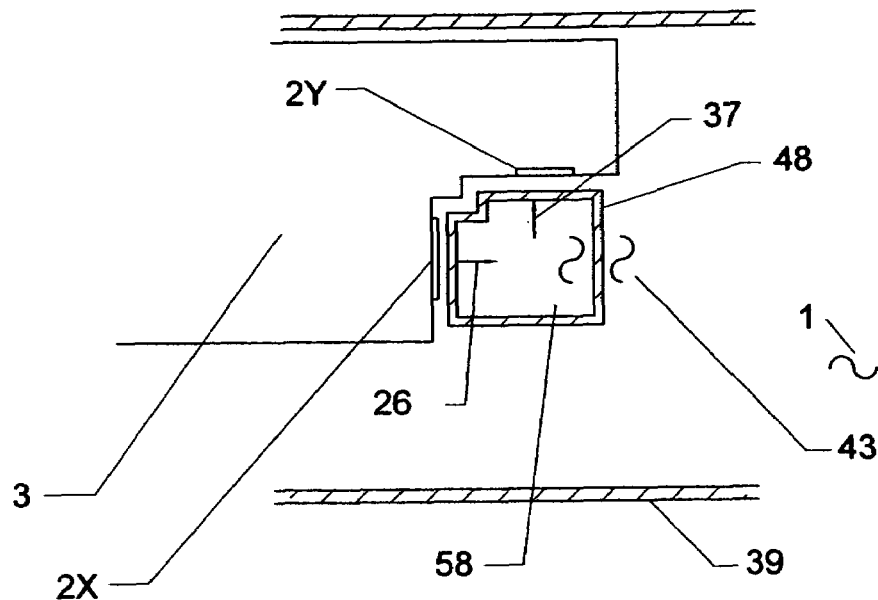
FIG. 17 depicts another section view of a calibration chamber in the calibration position.

FIG. 17 depicts the top view of the optional shaped, calibration chamber 48 in calibration position and the location of the nephelometric window light source module 2X and scattered light window module 2Y in the fluid 1 and sensor body 3. The source light beam 26 is directed into the calibration chamber 48 rather than rather than the sensing volume 43 of fluid 1 and is now being scattered by calibration material 58 resulting in scattered light beam 37.

Figure 18:
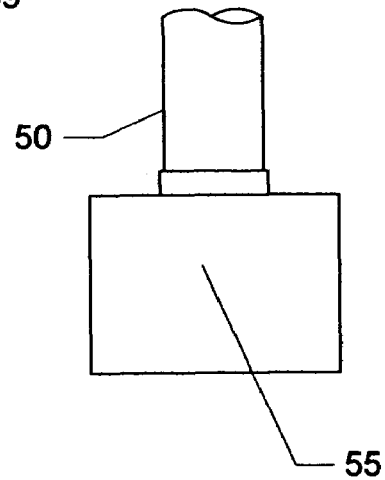
FIG. 18 depicts a solid block calibration component.

FIG. 18 depicts a solid calibration block 55 made of a low refractive index material and embedded with a known particle count material. Blocks of this type can be used as a calibration reference standard for EPA secondary calibration. Solid calibration block 55 is used in place of calibration chamber 48 and is automatically or manually inserted. Solid calibration block 55 is supported by shaft 50 and replaces calibration chamber 48 for non-regulatory reporting.

Figure 19:
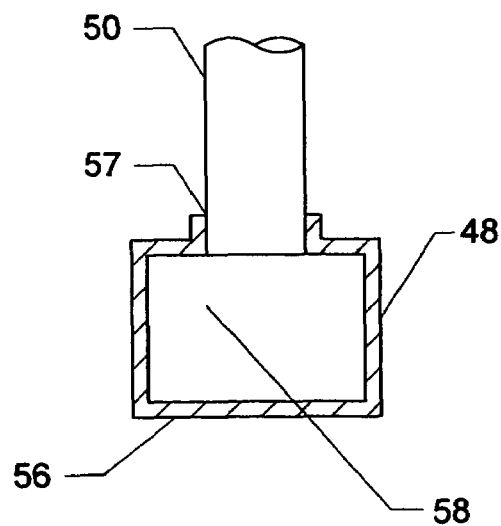
FIG. 19 depicts a section view of the calibration chamber.

FIG. 19 depicts an optional shaped, hollow chamber calibration chamber 48 with low refractive index walls 56 allowing accurate calibration and minimum impact of surface imperfections. The optional shaped calibration chamber 48 is filled and sealed through opening 57 with approved EPA stable calibration standard material 58. The calibration chamber 48 is supported by shaft 50.

Figure 20:
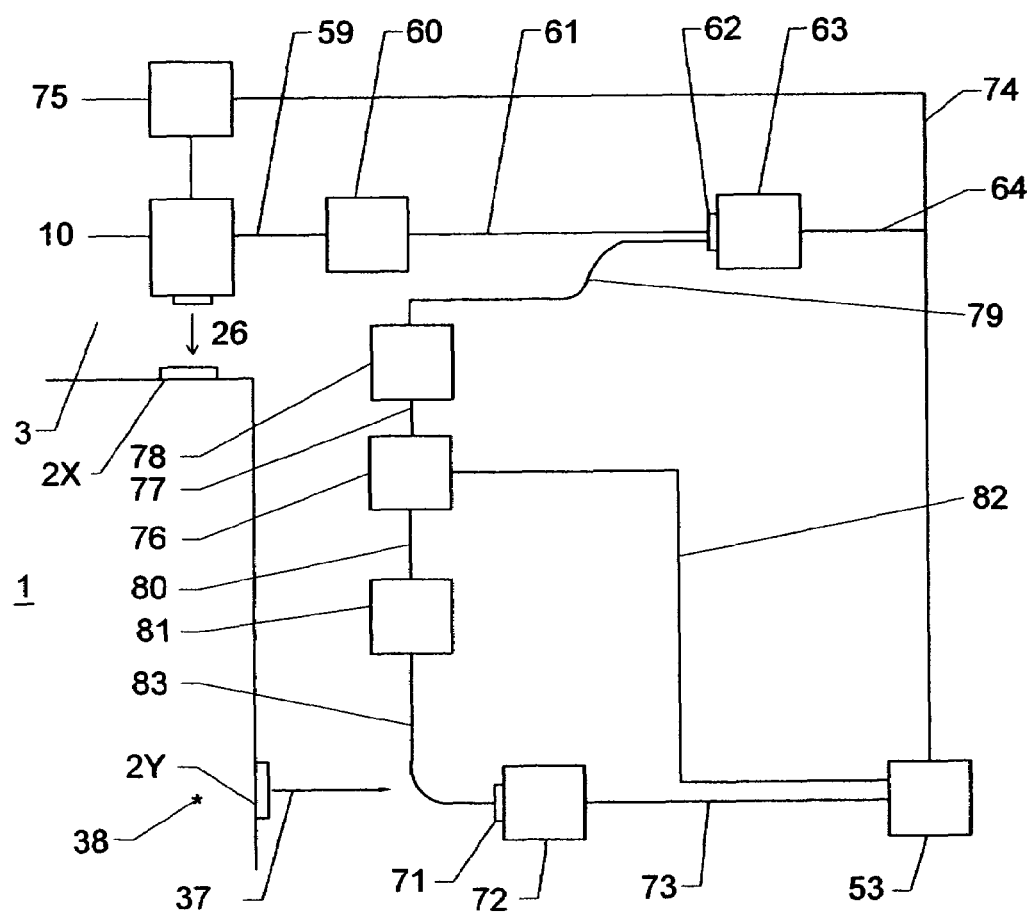
FIG. 20 depicts a schematic view of a self-check using a calibration light source.

FIG. 20 depicts the self-checking system using a separate calibration light source 76. A turbidity light source 10 emits a focused source light beam 26 from the sensor housing 3, through the light source window module 2X, and into the fluid 1 striking particles 38. The scattered light beam 37 from the particles 38 in the fluid 1 pass through the scattered light window module 2Y and are received in the scattered light detector 71 and scattered light receiver 72. The scattered light receiver 72 transmits information to the electronic circuit board 53 via the signal path 73.

The light source 10 also sends a portion of its light via light path 59 to an attenuator 60. Attenuator 60 may be of any value set by the design from zero attenuation on up. The light from attenuator 60 is transmitted by light path 61 to the reference light detector 62 and the reference light receiver 63. The reference light receiver 63 transmits information by signal path 64 to the electronic circuit board 53.

The calibration source light 76 is controlled by the electronic circuit board 53 via signal path 82. Emissions from the calibration source light 76 is sent by two light paths 77 and 80 to the attenuators 78 and 81, which may have set values of attenuation from zero on up depending on design. The light from attenuator 78 is transmitted via light path 79 to the reference light detector 62 and reference light receiver 63. The light from attenuator 81 is transmitted via light path 83 to the scattered light detector 71 and scattered light receiver 72. The signals from the reference light receiver 63 and the scattered light receiver 72 are transmitted by signal paths 64 and 73 respectively to the electronic circuit board 53.

By operating the calibration source 76 and allowing light to flow via light path 77, attenuator 78, and light path 79, a step increase in light is seen by the reference light detector 62 and reference light receiver 63 which transmits by signal path 64 to the electronic circuit board 53. Light also flows via light path 80, attenuator 81 and light path 83 to the scattered light detector 71 and scattered light receiver 72. The scattered light receiver 72 transmits a signal via signal path 73 to the electronic circuit board 53. The signals are compared with previous steps allowing a check of the scattered light detector 71, the scattered light receiver 72, the reference light detector 62, the reference receiver 63 and the electronic circuit board 53.

During normal operation with the calibration source light 76 off, the outputs of the reference receiver 63 and the scattered light receiver 72 are compared to get a measurement of the turbidity of the fluid 1. Additionally, a feed back loop from the reference receiver 63 via signal path 74 is optionally used to control the lamp controller 75, stabilizing the light source 10.

Figure 21:
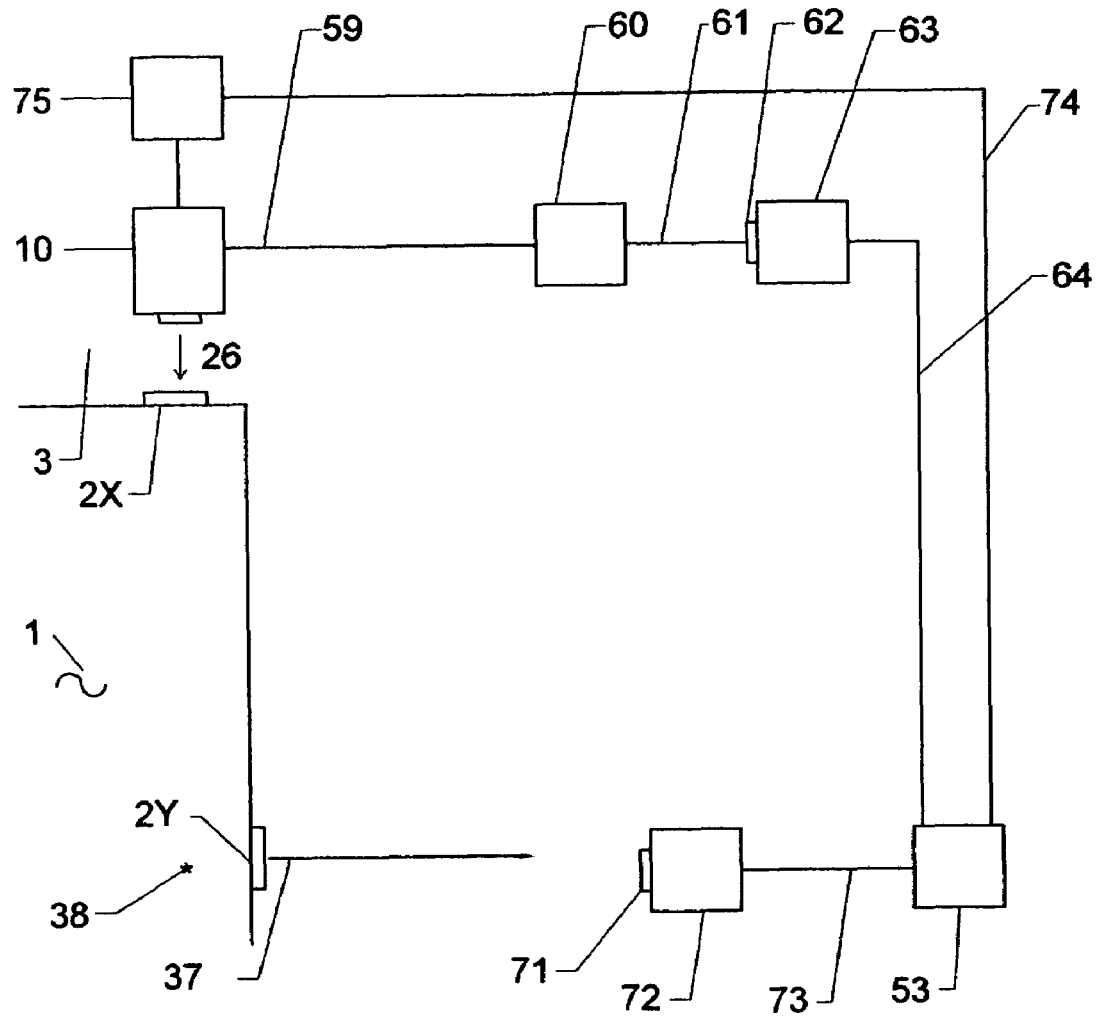
FIG. 21 depicts a schematic view of a self-check using light source change.

FIG. 21 depicts a self-check using a change in the output of light source 10, which emits a focused source light beam 26 through the sensor housing 3 through the source window module 2X and into the fluid 1 striking particles 38. The scattered light beam 37 from the particles 38 pass through the scattered light window module 2Y into the housing 3 and into the scattered light detector 71 and the scattered light receiver 72. The scattered light receiver 72 transmits a signal corresponding to turbidity information to the electronic circuit board 53 via the signal path 73.

The light source 10 also sends a portion of its light via light path 59 to attenuator 60. The attenuator 60 may be of any value from zero attenuation on up, depending on the design of the unit. The light from attenuator 60 is transmitted by light path 61 to the reference light detector 62 and the reference light receiver 63. The reference light receiver 63 transmits information to the electronic circuit board 53 via the signal path 64.

The electronic circuit board 53 using signal path 74 transmits a signal to the lamp controller 75 which controls the level of the light source 10. By forcing the light output to change a fixed amount from light source 10, the reference signal via light path 59, attenuator 60, light path 61, reference light detector 62, and reference light receiver 63 detects a set change in signal level which is sent to the electronic circuit board 53 by signal path 64. Similarly, a change in scattered light through the scattered light window module 2Y, the scattered light detector 71, and the scattered light receiver 72 detects a change in signal level which is sent via signal path 73 to the electronic circuit board 53. Although the signal in light path 59 and the scattered light beam 37 signal change, they are in lockstep. Since the light source 10 changes by a set amount, the individual components and their sensitivity may be checked by comparison to previous tests stored in the electronic circuit board 53.

During normal operation with the light source controller 75, not in check mode, the outputs of the reference receiver 63 and the scattered light receiver 72 are compared to get a measurement of the turbidity of the fluid 1. The signal from the reference light receiver 63 via the signal path 64 to the electronic circuit board 53 is used as a portion of a feedback in which the electronic circuit board 53 holds the light source constant from light source 10 via signal path 74, and lamp controller 75.

Figure 22:
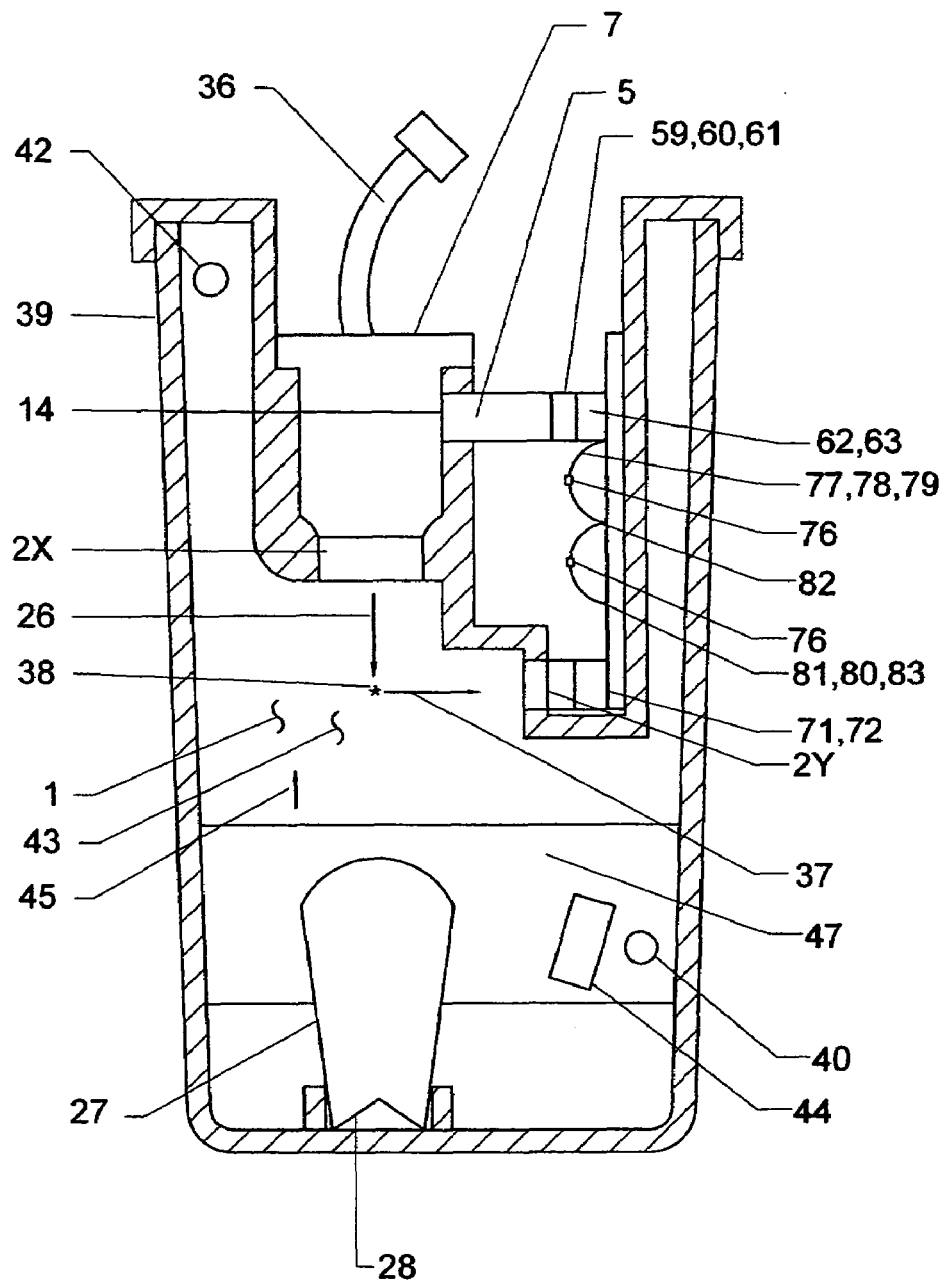
FIG. 22 depicts a section view of said nephelometer and sensor with calibration light source.

FIG. 22 depicts a section view of said nephelometric sensor with calibration light source 76. Fluid 1 enters exterior container 39 at inlet 40 where it is directed against bubble separator device 44. The bubble free fluid 45 portion of fluid is directed downward by fluid separator plate 47. The bubble free fluid 45 then flows through the sensing volume 43 and out through main outlet 42. The source light beam 26 from light source 10 in lamp module 7 exits the sensor housing 3 through the light source window module 2X and contacts particle 38 in sensing volume 43 generating scattered light beam 37. Scattered light beam 37 enters scattered light sensor window module 2Y going to scattered light detector 71 and scattered light receiver 72. The remaining light source beam 26 continues onward entering the tapered cone light trap consisting of tapered cylinder 27 typical shown and cone diffuser 28 typical shown. A portion of the light from light source 10 is directed through sensor light path opening 5, light path opening 14, light path 59, attenuator 60 and light path 61 to the reference light detector 62 and reference light receiver 63. The light source 10 type of light emitter is indexed by connector 36. Calibration source light 76 sends light via light path 80, attenuator 81, and light path 83 to light detector 71 by light path 77, attenuator 78 and light path 79 to the reference light detector 62. The calibration source light 76 is controlled via signal path 82. When calibration source light 76 is energized, a step in signal is detected by scattered light detector 71 and reference light detector 62, which is compared to previous measurements.

The above described embodiments are set forth by way of example and are not for the purpose of limiting the present invention. It will be apparent to those skilled in the art that obvious modifications, derivations and variations can be made to the embodiments without departing from the scope of the invention. Accordingly, the claims appended hereto should be read in their full scope including any such modifications, derivations and variations.

What is claimed is:

1. A nephelometric turbidity sensor device for measuring solid particle concentrations in a fluid comprising:

A double walled structure having an light-tight exterior container and one or more fluid-tight light-tight housings, wherein the structure incorporates light receiving and light emitting elements;

said light-tight exterior container to contain a fluid to be measured and having a fluid inlet and at least one fluid outlet to provide fluid flow through the container, and having a non-reflective inner surface;

said fluid-tight light-tight housing having a lamp module comprising a light source that generates a focused light beam, and transparent window module;

a first optical element for focusing and directing the light emitted from the light source through a window module into the to-be-measured fluid;

a second optical element, for collecting a portion of scattered light which is generated when the focused light beam strikes particles in the fluid in the container, directs said collected scattered light onto a scattered light detector;

said scattered light detector converts incident light to an electrical signal and transmits it to the scattered light receiver which transforms the electrical signal for further processing;

an electronic circuit board that further processes electrical signals from the scattered light detector and scattered light receiver;

wherein the improvement is: said nephelometric turbidity device comprises a combination of multiple absorbing and reflective elements for attenuation of extraneous scattered light signals.

2. A nephelometric turbidity device, in accordance with claim 1, further comprising:

Said light attenuation means is located within said exterior container and opposite the light source window module and out of view of a second light focusing element, wherein the light attenuation element further comprises a tapered cylinder of a non-reflective material to receive the light beam from the light source and to direct it onto a light absorbing diffuser cone which redirects any remaining light onto the walls of the tapered cylinder to eliminate unwanted extraneous light signals.

3. A nephelometric turbidity sensor device for measuring solid particle concentrations in a fluid comprising:

A double walled structure having an light-tight exterior container and one or more fluid-tight light-tight housings, wherein the structure incorporates light receiving and light emitting elements;

said light-tight exterior container to contain a fluid to be measured and having a fluid inlet and at least one fluid outlet to provide fluid flow through the container, and having a non-reflective inner surface;

said fluid-tight light-tight housing having a lamp module comprising a light source that generates a focused light beam, and transparent window module;

a first optical element for focusing and directing the light emitted from the light source through a window module into the to-be-measured fluid;

a second optical element, for collecting a portion of scattered light which is generated when the focused light beam strikes particles in the fluid in the container, directs said collected scattered light onto a scattered light detector;

said scattered light detector converts incident light to an electrical signal and transmits it to the scattered light receiver which transforms the electrical signal for further processing;

an electronic circuit board that further processes electrical signals from the scattered light detector and scattered light receiver;

wherein the improvement is: said nephelometric turbidity device comprises a fluid separator plate located within said exterior container for attenuation of non-particle signals arising from entrained gasses and bubbles in said fluid.

4. A nephelometric turbidity device, in accordance with claim 3, further comprising:

Said fluid separator plate that is angled into the flow of the fluid to separate the fluid to-be-measured into segments of fluid containing gasses or bubbles and segments of fluid which are bubble free, which said bubble free segment is then directed by said fluid separator plate through said sensing volume.

5. A nephelometric turbidity sensor device for measuring solid particle concentrations in a fluid comprising:

A double walled structure having an light-tight exterior container and one or more fluid-tight, light-tight housings, wherein the structure incorporates light receiving and light emitting elements;

said light-tight exterior container to contain a fluid to be measured and having a fluid inlet and at least one fluid outlet to provide fluid flow through the container, and having a non-reflective inner surface;

said fluid-tight light-tight housing having a lamp module comprising a light source that generates a focused light beam, and transparent window module;

a first optical element for focusing and directing the light emitted from the light source through a window module into the to-be-measured fluid;

a second optical element, for collecting a portion of scattered light which is generated when the focused light beam strikes particles in the fluid in the container, directs said collected scattered light onto a scattered light detector;

said scattered light detector converts incident light to an electrical signal and transmits it to the scattered light receiver which transforms the electrical signal for further processing;

an electronic circuit board that further processes electrical signals from the scattered light detector and scattered light receiver;

wherein the improvement is: said window module of said nephelometric turbidity device is constructed with multiple optical elements for attenuation of window fogging.

6. A nephelometric turbidity device, in accordance with claim 5:

Wherein said window module comprises multiple transparent optical elements sealed and separated to eliminate concentration of moisture on the interior of said window module.

7. A nephelometric turbidity device, in accordance with claim 5:

Wherein said sealed and separated transparent elements are further separated by a dry interior zone filled with either a dry gas or a vacuum.

8. A nephelometric turbidity sensor device for measuring solid particle concentrations in a fluid comprising:

A double walled structure having an light-tight exterior container and one or more fluid-tight, light-tight housings, wherein the structure incorporates light receiving and light emitting elements;

said light-tight exterior container to contain a fluid to be measured and having a fluid inlet and at least one fluid outlet to provide fluid flow through the container, and having a non-reflective inner surface;

said fluid-tight light-tight housing having a lamp module comprising a light source that generates a focused light beam, and transparent window module;

a first optical element for focusing and directing the light emitted from the light source through a window module into the to-be-measured fluid;

a second optical element, for collecting a portion of scattered light which is generated when the focused light beam strikes particles in the fluid in the container, directs said collected scattered light onto a scattered light detector;

said scattered light detector converts incident light to an electrical signal and transmits it to the scattered light receiver which transforms the electrical signal for further processing;

an electronic circuit board that further processes electrical signals from the scattered light detector and scattered light receiver;

wherein the improvement is: said nephelometric turbidity device comprises a means for automatic indexing of said light sources, which are interchangeable, with a corresponding algorithm in a single housing.

9. A nephelometric turbidity device, in accordance with claim 8, further comprising:

A means for interchangeable light sources further comprising light source types which include incandescent, LED, OLED, laser or other light emitting elements.

10. A nephelometric turbidity sensor device for measuring solid particle concentrations in a fluid comprising:

A double walled structure having an light-tight exterior container and one or more fluid-tight, light-tight housings, wherein the structure incorporates light receiving and light emitting elements;

said light-tight exterior container to contain a fluid to be measured and having a fluid inlet and at least one fluid outlet to provide fluid flow through the container, and having a non-reflective inner surface;

said fluid-tight light-tight housing having a lamp module comprising a light source that generates a focused light beam, and transparent window module;

a first optical element for focusing and directing the light emitted from the light source through a window module into the to-be-measured fluid;

a second optical element, for collecting a portion of scattered light which is generated when the focused light beam strikes particles in the fluid in the container, directs said collected scattered light onto a scattered light detector;

said scattered light detector converts incident light to an electrical signal and transmits it to the scattered light receiver which transforms the electrical signal for further processing;

an electronic circuit board that further processes electrical signals from the scattered light detector and scattered light receiver;

wherein the improvement is: said nephelometric turbidity device comprises a calibration standard material for validation of a measurement response for automatic verification of operation using self calibration.

11. The device, in accordance with claim 10, further comprises:

A moveable solid block of known calibration material which is automatically inserted through said external container wall and placed in said sensing volume for detection for automatic self calibration.

12. The device, in accordance with claim 10, further comprises:

A regulatory approved calibration standard material which is automatically inserted through said external container wall and placed in said volume for detection.

13. A nephelometric turbidity sensor device for measuring solid particle concentrations in a fluid comprising:

A double walled structure having an light-tight exterior container and one or more fluid-tight, light-tight housings, wherein the structure incorporates light receiving and light emitting elements;

said light-tight exterior container to contain a fluid to be measured and having a fluid inlet and at least one fluid outlet to provide fluid flow through the container, and having a non-reflective inner surface;

said fluid-tight light-tight housing having a lamp module comprising a light source that generates a focused light beam, and transparent window module;

a first optical element for focusing and directing the light emitted from the light source through a window module into the to-be-measured fluid;

a second optical element, for collecting a portion of scattered light which is generated when the focused light beam strikes particles in the fluid in the container, directs said collected scattered light onto a scattered light detector;

said scattered light detector converts incident light to an electrical signal and transmits it to the scattered light receiver which transforms the electrical signal for further processing;

an electronic circuit board that further processes electrical signals from the scattered light detector and scattered light receiver;

wherein the improvement is: said nephelometric turbidity device comprises a stepped light means for self check of said reference light detector, said reference light receiver, said scattered light detector, said scattered light receiver, and said electronic circuit board.

14. The device, in accordance with claim 13, further comprising:

A means for generating a step of a known degree in the source light with results to be compared with previous measurement data.

15. The device, in accordance with claim 13, further comprises:

A means for stepped increase in the light received by said reference light detector and said scattered light detector by transmitting a sample of light from the calibration source light to the detectors, with results to be compared with previous measurement data.

* * * * *